United States Patent
Yacoby

(10) Patent No.: US 6,430,256 B1
(45) Date of Patent: Aug. 6, 2002

(54) DIRECT STRUCTURE DETERMINATION OF SYSTEMS WITH TWO DIMENSIONAL PERIODICITY

(75) Inventor: Yizhak Yacoby, Bizaron (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 09/845,242

(22) Filed: Apr. 30, 2001

(51) Int. Cl.[7] ............................................... G01N 23/20
(52) U.S. Cl. ............................ 378/71; 378/73; 378/53; 378/76; 378/70
(58) Field of Search .............................. 378/53, 51, 73, 378/70, 71, 76

(56) References Cited

U.S. PATENT DOCUMENTS

| | | | | |
|---|---|---|---|---|
| 5,426,678 A | * | 6/1995 | Terhune et al. ............. | 376/249 |
| 5,867,276 A | * | 2/1999 | McNeil et al. ............... | 356/445 |
| 6,005,913 A | * | 12/1999 | Zombo et al. ................ | 378/71 |

OTHER PUBLICATIONS

Baltes et al., "Measurement of the X-ray diffraction phase in a 2D crystal" Phys. Rev. Lett. 79:1285–8 (1997).
DeSantis et al., "Anomalous X-ray diffraction of a hexagonal Fe/Ru superlattice" Phys. Rev. B 46:15 465–71 (1992).
Miceli, "X-ray reflectivity from heteroepitaxial layers Semiconductor Interfaces, Microstructures and Devices: Properties and Applications" pp 87–114 (Bristol: Institute of Physics Publishing 1993).
Morelhao et al. "Structural properties of heteroepitaxial systems using hybrid multiple diffraction in Renninger scans" J. Appl. Phys. 73:4218–26 (1993).
Rius et al., "A tangent formula derived from Patterson–function arguments. IV. The solution of difference structures directly from superstructure reflections" Acta Crystallogr. A 52:634–9 (1996).

Robinson et al., "Surface X-ray diffraction" Rep. Prog. Phys 55:599–651 (1992).
Sanyal et al., "Fourier reconstruction of density profiles of thin films using anomalous X-ray reflectivity" Europhys. Lett. 21:691–6 (1993).
Sinha et al., "X-ray scattering studies of surface roughness of Ga As/AlAs multilayers" Physica B 198:72–7 (1994).
Tegze et al., "X-ray holography with atomic resolution" Nature 380:49–51 (1996).
Torrelles et al., "Application of X-ray direct methods to surface reconstructions: the solution of projected superstructures" Phys. Rev. B57:R 4281–4 (1998).
Torrelles et al., "Application of the 'direct methods' difference sum function to the solution of reconstructed surfaces" Surf. Sci. 423:2–3 (1999).
Yacoby et al., "Direct Structure determination of systems with two dimensional periodicity" J. Phys: Condens. Matter 12:3929–3938 (2000).
Yacoby, "Structure factor amplitude and phase determination by a new two beam diffraction interference method" Solid State Commun. 91:529–33 (1994).
Zegenhagen, "Surface structure determination with X-ray standing waves" Surf. Sci. Rep. 18:199–271 (1993).

* cited by examiner

*Primary Examiner*—David V. Bruce
*Assistant Examiner*—Pamela R Hobden
(74) *Attorney, Agent, or Firm*—Hamilton, Brook, Smith & Reynolds, P.C.

(57) ABSTRACT

A method is disclosed for determining the three-dimensional atomic structure of systems that are periodic in two dimensions, a-periodic in the third dimension, and are commensurate with an underlying three-dimensional crystal. The system is considered as composed of two components: an unknown system periodic in two dimensions, a-periodic in the third with an unknown structure and a known system also periodic in two dimensions with a known structure. The two systems are commensurate with each other. The method provides the structure of the unknown and therefore of the entire system.

11 Claims, 7 Drawing Sheets

DIRECT STRUCTURE DETERMINATION OF SYSTEMS WITH TWO DIMENSIONAL PERIODICITY

FIELD OF THE INVENTION

The present invention relates to determining atomic structure using x-ray techniques. More specifically, the invention relates to an x-ray method for the determination of the structure of systems that have two-dimensional periodicity and are positionally correlated with an underlying substrate crystal.

BACKGROUND OF THE INVENTION

Many systems of current interest, both from a scientific and technological standpoint, can be characterized as two-dimensional crystals. Such systems are fully or partially periodic in two dimensions, a-periodic in the third, and positionally correlated with an underlying substrate crystal. Examples include reconstructed crystal surfaces, layered heterostructures, crystalline-amorphous interfaces (e.g., Si—$SiO_2$), and self-assembled systems crystallized on a substrate. These systems are interesting because their physical properties differ markedly from those of bulk materials. Their study has been hampered by a lack of characterization tools that can probe these types of systems with atomic resolution.

Various x-ray methods have been used to investigate 2D structures. These include reflectivity and diffuse scattering (Sinha S K, et.al. 1994 X-ray scattering studies of surface roughness of Ga As/AlAs multilayers Physica B 198 72–7; and Miceli P F 1993 X-ray reflectivity from heteroepitaxial layers Semiconductor Interfaces, Microstructures and Devices: Properties and Applications (Bristol: Institute of Physics Publishing) pp 87–114), high-resolution x-ray diffraction along Bragg and truncation rods (Robinson I K and Tweet D J 1992 Surface X-ray diffraction Rep. Prog. Phys 55 599–651), multiple diffraction (Morelhao S L and Cardoso L P 1993 Structural properties of heteroepitaxial systems using hybrid multiple diffraction in Renninger scans J. Appl. Phys. 73 4218–26), and standing waves (Zegenhagen J 1993 Surface structure determination with X-ray standing waves Surf. Sci. Rep. 18 7–8). In all these methods, it is necessary to first postulate a structural model and then refine its parameters to obtain the best fit with experiment. Thus, if the model is incorrect, the structure will necessarily be incorrect.

Interface structures are often quite complex and guessing a reasonable structural model can be both difficult and unreliable. Two direct methods, proposed in the past, are anomalous reflectivity (Sanyal M K, et.al. 1993 Fourier reconstruction of density profiles of thin films using anomalous X-ray reflectivity Europhys. Lett.21 691–6) and x-ray holography (Tegze M and Faigel G 1996 X-ray holography with atomic resolution Nature 380 49–51). These methods are of limited use for 2D structures. The former only provides in-plane-averaged results. The latter provides the average structure around probe atoms that are typically located at in equivalent sites. In special cases when the system has inversion symmetry, the problem is greatly simplified because the scattering factors are real. This has been utilized to obtain the scattering factors of Fe/Ru superlattices and to calculate their structure by Fourier back-transformation (De S M, De A A, Raoux D, Maurer M, Ravet M F and Piecuch M 1992 Anomalous X-ray diffraction of a hexagonal Fe/Ru superlattice Phys. Rev. B 46 15 465–71).

Recently, using the tangent formula of Rius et al. (Rius J, Miravitlles C and Allman R 1996 A tangent formula derived from Patterson-function arguments. IV. The solution of difference structures directly from superstructure reflections Acta Crystallogr. A 52 634–9 ), Torrelles et al. (Torrelles X, et. al. 1998 Application of X-ray direct methods to surface reconstructions: the solution of projected superstructures Phys. Rev. B57 R 4281–4) developed a method for obtaining directly the projection of a reconstructed crystal surface on the surface plane from the Bragg-rod diffraction intensities on the equatorial plane in reciprocal space. The method has been generalized (Torrelles, et. al. 1999 Application of the "direct methods" difference sum function to the solution of reconstructed surfaces Surf. Sci. 423 2–3) to obtain the three-dimensional structure using the intensities on additional points along the Bragg rods. The problem of this method is that it involves the refinement of a large number of phase angles. Thus, the computation complexity grows at least as the square of the number of atoms.

It is therefore an object of this invention to provide a method for the determination of the structure of systems that have two-dimensional periodicity and are positionally correlated with an underlying substrate crystal that is much simpler than the methods of the prior art.

It is another object of this invention to provide a method for direct determination of the structure of systems that have two-dimensional periodicity and are positionally correlated with an underlying substrate crystal that does not require an a priori correct conjecture of the structure.

It is yet another object of this invention to provide a method for direct determination of the structure of systems that have two-dimensional periodicity and are positionally correlated with an underlying substrate crystal that is general and does not depend on the symmetry properties of the system.

It is a further object of this invention to provide a method for direct determination of the structure of systems that have two-dimensional periodicity and are positionally correlated with an underlying substrate crystal that provides the three dimensional structure of the system.

It is yet an additional object of this invention to provide a method for direct determination of the structure of systems that have two-dimensional periodicity and are positionally correlated with an underlying substrate crystal whose computational complexity scales linearly with the number of atoms.

Further objects and advantages of this invention will appear as the description proceeds.

SUMMARY OF THE INVENTION

The present invention is directed to a general method for determining the three-dimensional structure of systems that are periodic in two dimensions, a-periodic in the third, and are commensurate with an underlying three-dimensional crystal. The system is considered as composed of two components: an "unknown system" periodic in two dimensions, a-periodic in the third with an unknown structure and a "known system" also periodic in two dimensions with a known structure. The two systems are commensurate with each other. The sum of their electron densities is equal to the electron density of the entire system. The method provides the structure of the unknown and therefore of the entire system. The structure the method provides does not depend on an a priori correct model of the structure, can handle systems with large 2D unit cells and large layer thickness, and is non-destructive. Using diffraction data along one Bragg rod, the system layer structure can be reconstructed with monolayer resolution; and the full three-dimensional structure of a system can be reconstructed with atomic resolution from diffraction data along the Bragg rods within a certain volume in reciprocal space.

In a first aspect, the present invention is directed towards providing an x-ray method for the determination of the structure of systems that have two-dimensional periodicity and are positionally correlated with an underlying substrate crystal comprising the following steps:

creating two overlapping x-ray beams in the system having two-dimensional periodicity such that the overlapping beams propagate at an angle with respect to each other and their orientation relative to the two-dimensional system is such that the diffracted beams interfere with each other;

Measuring the diffraction intensity and diffraction interference patterns;

determining the phase derivative of the total complex scattering factor (CSF) along the Bragg rods using the diffraction interference patterns;

determining the CSF along the Bragg rods from the measured diffraction intensity, the phase derivative of the total CSF, and the CSF of the known system;

determining the electron-density function of the layer structure of the system by Fourier transforming the CSF along one Bragg rod;

performing a three-dimensional Fourier back-Transform into real space to provide the three-dimensional real space x-ray dielectric function; and determining the three-dimensional spatial structure, of the system having two-dimensional periodicity from the three-dimensional x-ray dielectric function.

In the method of the experiment, the phase derivative of the total CSF is measured by employing the two-beam diffraction interference method (Yacoby Y 1994 Structure Factor amplitude and phase determination by a new two beam diffraction interference method Solid State Commun. 91 529–33 and Baltes H, Yacoby Y, et.al. 1997 Measurement of the X-ray diffraction phase in a 2D crystal Phys. Rev. Lett. 79 1285–8). The phase is then determined by either direct integration or preferably by an iterative method using the measured diffraction amplitudes, the phase derivative of the CSF, and the CSF of the known system.

In another aspect, the present invention is directed towards providing an x-ray method for the determination of the structure of systems that have two-dimensional periodicity, are positionally correlated with an underlying substrate crystal, and wherein the CSF of the unknown system varies slowly along the Bragg rods compared to that of the known system comprising the following steps:

Measuring the diffraction intensity along the Bragg rods;

locating the zero point of the real space z-coordinate such that changes in the CSF of the unknown system for two adjacent points along a Bragg rod are negligible compared to the changes in the CSF of the known system for the corresponding points;

determining the CSF along the Bragg rods from the measured diffraction intensity patterns and the CSF of the known system;

determining the electron-density function of the layer structure of the system by Fourier transforming the CSF along one Bragg rod;

performing a three-dimensional Fourier back-Transform into real space to provide the three-dimensional real space x-ray dielectric function; and determining the three-dimensional spatial structure, of the system having two-dimensional periodicity from the three-dimensional x-ray dielectric function.

In this aspect of the invention, wherein, in addition, the thickness of the unknown structure having two-dimensional periodicity is small compared to its distance from the system surface, then the zero point of the real space z-coordinate is preferably placed within the unknown two-dimensional layer.

In a further aspect, the invention is directed towards providing an x-ray method for the determination of the periodic component of the structure of systems that have partial two-dimensional periodicity, are positionally correlated with an underlying substrate crystal, comprising the following steps:

creating two overlapping x-ray beams in the system having two-dimensional periodicity such that the overlapping beams propagate at an angle with respect to each other and their orientation relative to the two-dimensional system is such that the diffracted beams interfere with each other;

Measuring the diffraction intensity and diffraction interference patterns;

determining the phase derivative of the total complex scattering factor (CSF) along the Bragg rods using the diffraction interference patterns;

determining the CSF along the Bragg rods from the measured diffraction intensity, the phase derivative of the total CSF, and the CSF of the known system;

determining the electron-density function of the layer structure of the system by Fourier transforming the CSF along one Bragg rod;

performing a three-dimensional Fourier back-Transform into real space to provide the three-dimensional real space x-ray dielectric function; and determining the three-dimensional spatial structure, of the system having two-dimensional periodicity from the three-dimensional x-ray dielectric function.

In yet a further aspect, the invention is directed towards providing an x-ray method for the determination of the periodic component of the structure of systems that have partial two-dimensional periodicity, are positionally correlated with an underlying substrate crystal, and wherein the CSF of the unknown system varies slowly along the Bragg rods compared to that of the known system comprising the following steps:

Measuring the diffraction intensity along the Bragg rods;

locating the zero point of the real space z-coordinate such that changes in the CSF of the unknown system for two adjacent points along a Bragg rod are negligible compared to the changes in the CSF of the known system for the corresponding points;

determining the CSF along the Bragg rods from the measured diffraction intensity patterns and the CSF of the known system;

determining the electron-density function of the layer structure of the system by Fourier transforming the CSF along one Bragg rod;

performing a three-dimensional Fourier back-Transform into real space to provide the three-dimensional real space x-ray dielectric function; and determining the three-dimensional spatial structure, of the system having two-dimensional periodicity from the three-dimensional x-ray dielectric function.

In this aspect of the invention, wherein, in addition, the thickness of the unknown structure having partial two-dimensional periodicity is small compared to its distance from the system surface, then the zero point of the real space z-coordinate is preferably placed within the unknown two-dimensional layer.

According to the method of the invention, the two overlapping x-ray beams in the structure having two-dimensional periodicity, or partial two dimensional periodicity, are obtained by total external reflection from a heavy metal film on the sample surface.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The method of the invention is quite general but is most easily described in terms of a typical but non-limitative example. The system shown in FIG. 1 has been chosen to illustrate the first aspect of the invention. The system is composed of a three-dimensional semi-infinite crystal, GaAs 34, containing embedded crystalline monolayers of AlAs 35. The incident 31, reflected 32, and diffracted 33 X-ray beams are schematically shown, as is a gold reflecting layer deposited on the upper layer of the GaAs.

The electron density of the unknown 2D system is the difference between the ideal semi-infinite GaAs crystal considered to be the known system and the actual sample. If the GaAs is distorted, relative to its ideal structure, then the difference between the actual and ideal structure is also part of the unknown 2D system.

Figure 2:
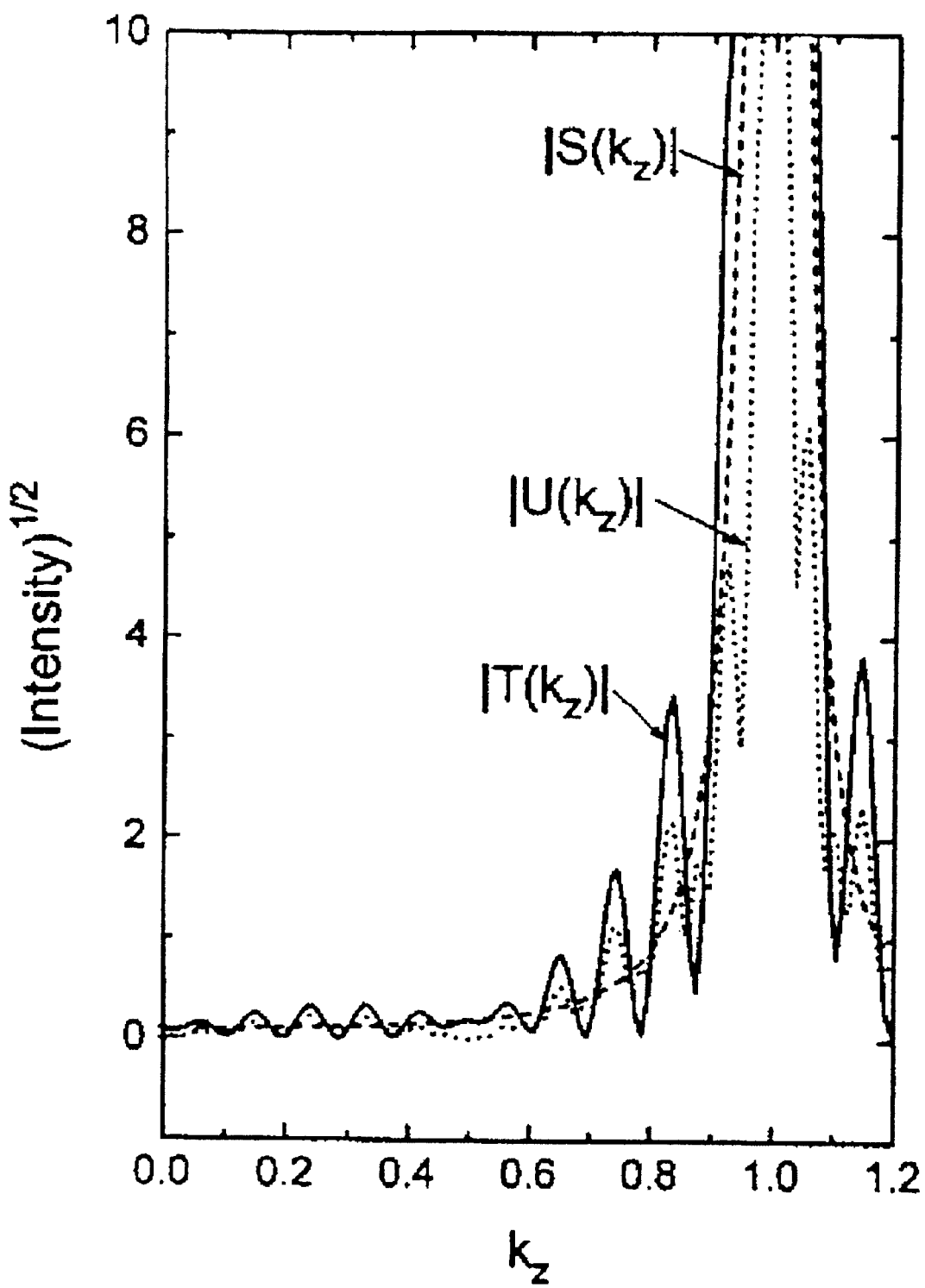
FIG. 2 shows an example of the moduli of the complex scattering factors of the sample of FIG. 1.

The 3D crystalline lattice (GaAs) defines a two-dimensional grid on x-y planes parallel to the interface. First consider a 2D structure that is fully periodic with respect to this grid. The complex scattering factor (CSF) of the ideal semi-infinite crystal, $S(k_z)$, is known and non-zero along a set of Bragg (truncation) rods which are oriented parallel to the surface normal (z-axis). The CSF of the unknown 2D system, $U(k_z)$, also contributes to the scattering intensity along these Bragg rods. Since the transverse and longitudinal coherence lengths of the incident x-ray beam are much larger than the thickness of the unknown 2D structure (Yacoby Y 1994 Structure Factor amplitude and phase determination by a new two beam diffraction interference method Solid State Commun. 91 529–33 and Baltes H, Yacoby Y, et.al. 1997 Measurement of the X-ray diffraction phase in a 2D crystal Phys. Rev. Lett.79 1285–8), the contributions from the known and unknown systems interfere with each other coherently and the measured diffraction intensity is proportional to the absolute value squared of the total $CSF|T(k_z)|^2=|S(k_z)+U(k_z)|^2$. The moduli of the three CSFs, over a fraction of a Bragg rod, are shown in FIG. 2 for a representative data set. For the purpose of illustration, the curves shown in FIG. 2 are calculated using a simulated data set based on the known atomic structures of GaAs and AlAs and assuming a sample consisting of four monolayers of AlAs buried twenty monolayers beneath the surface of the GaAs.

The method of the invention has two embodiments. The first embodiment is generally applicable and consists of two steps. First the phase derivative $\partial\phi/\partial k_z$ of the total CSF along the Bragg rods is determined. This is accomplished using the two-beam diffraction interference method described in the above referenced papers by Yacoby Y and by Baltes H, Yacoby Y, et.al. A thin gold film is evaporated on the sample. A monochromatic x-ray beam enters the sample from the side (see FIG. 1) and, since gold is a heavy atom, it undergoes, at small incidence angles, total external reflection. Under these conditions, the incident and reflected beams are diffracted in pairs of coherent and exactly parallel beams. The beams in each pair interfere with each other coherently, providing the phase derivative along the Bragg rods.

The second step is to determine the phase itself. In principle, the measured phase derivative could be integrated. However, in order to perform the integration, it is necessary to know the absolute phase at least at one point on each Bragg rod. In addition, even a small amount of noise in the experimental data produces large errors in the phase, rendering it useless. Therefore, in practice, some other method must be devised to determine the phase.

The method of the invention makes use of an iterative approach that determines the phase from the measured diffraction intensity along the Bragg rods the phase derivative itself and the CSF of the ideal GaAs semi-infinite crystal without the need for integration. First consider two points along a Bragg rod at a small separation $\Delta k_z$ from each other. The total CSFs at the two points can be expressed in terms of the CSF of the known system and the unknown CSF as follows:

$$S_1+U_1=|T_1|e^{i\Phi_1} \qquad (1)$$

$$S_2+|Q|e^{i\Phi_Q}U_1=|T_2|e^{i(\Phi_1+\Delta)} \qquad (2)$$

Here, indices 1 and 2 correspond to $k_z$ and $k_z+\Delta k_z$, respectively, $$S=|S|e^{i\Phi_S} \text{ and } U=|U|e^{i\Phi_U}$$

Q is the complex ratio between $U_2$ and $U_1$, and $\Delta=\Phi_2-\Phi_1$. $|T|$ and $\Delta$ are directly determined from the experimentally measured scattering intensity and phase derivative, and S is the known CSF of the semi-infinite ideal GaAs crystal. Now approximate $|Q|\sim 1$ and equations (1) and (2) are solved for $U_1$, $\Phi_1$ and $\Phi_Q$. At each point $k_z$ there are two solutions. The correct solution is determined from the requirement that $U_1$ should vary smoothly along the Bragg rod. In this way $U_1$ can be calculated for all values of $k_z$. Now the function $U(k_z)$ is used to calculate a better approximation for $|Q|$ and to iterate again the solution of equations (1) and (2). In all of the simulations carried out to test the method of the invention, this procedure converged after less than six iterations (Yacoby Y, et.al. 2000 Direct Structure determination of Systems with two dimensional periodicity. J.Phys: Condens. Matter 12 3929–3938).

Figure 3A:
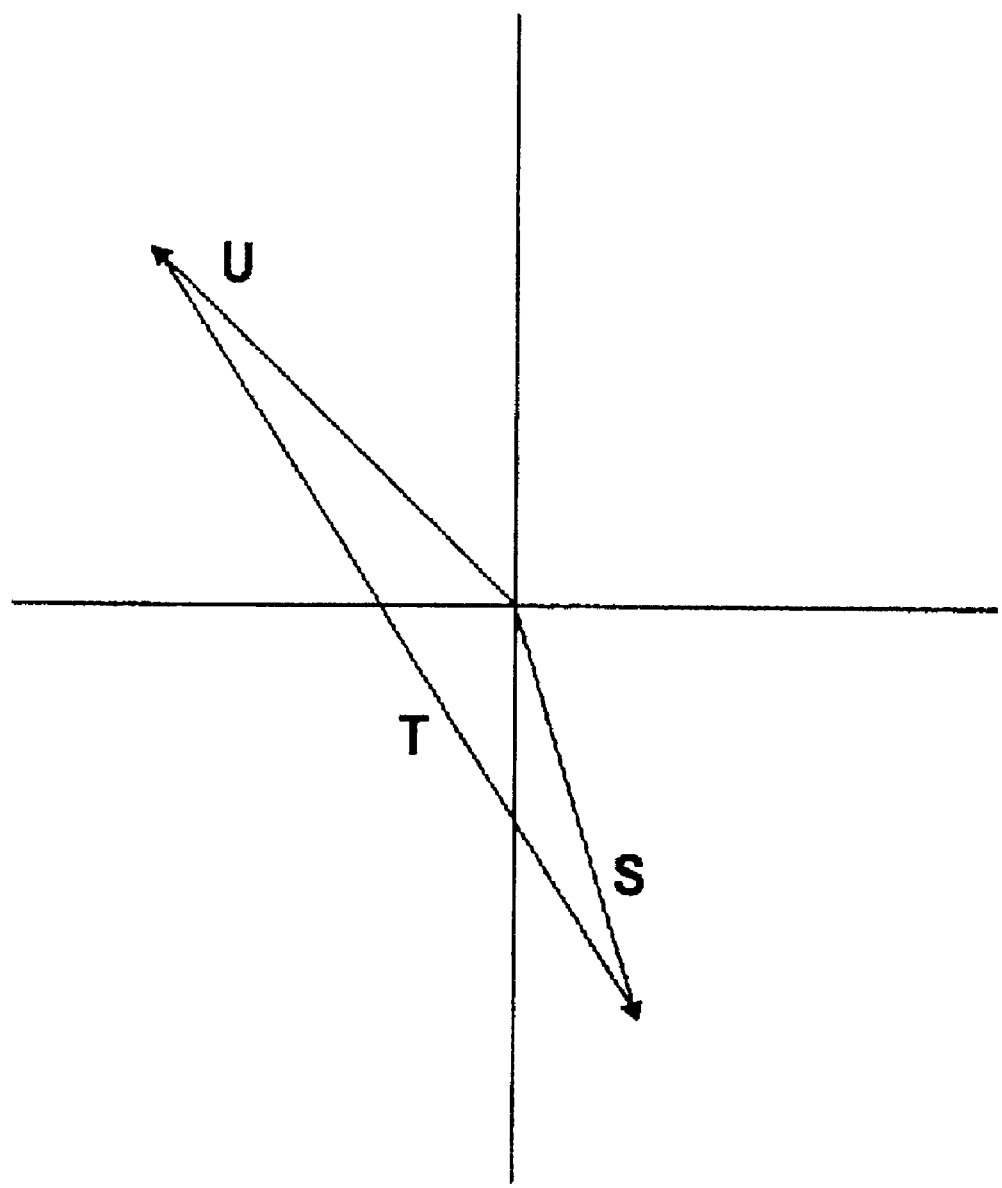
FIG. 3A shows a graphic representation on the complex plane of the complex scattering factors at a single point along a Bragg rod.
Figure 3B:
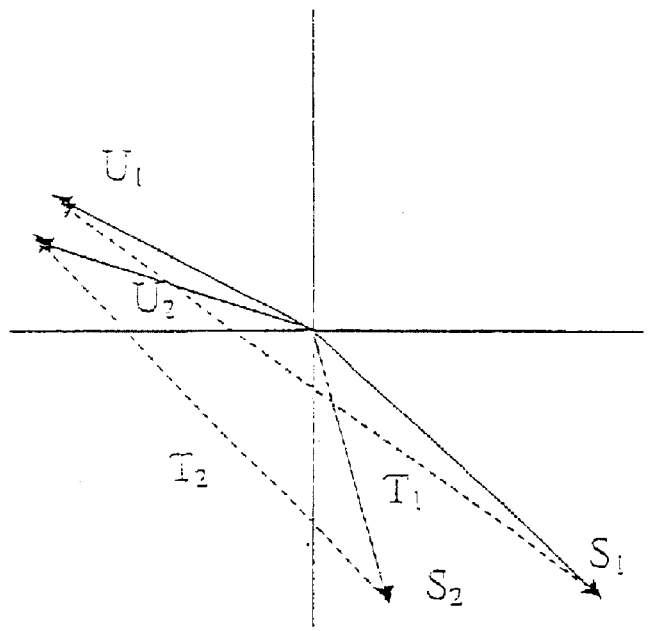
FIG. 3B shows a graphic representation on the complex plane of the complex scattering factors at two adjacent points along a Bragg rod.
Figure 3C:
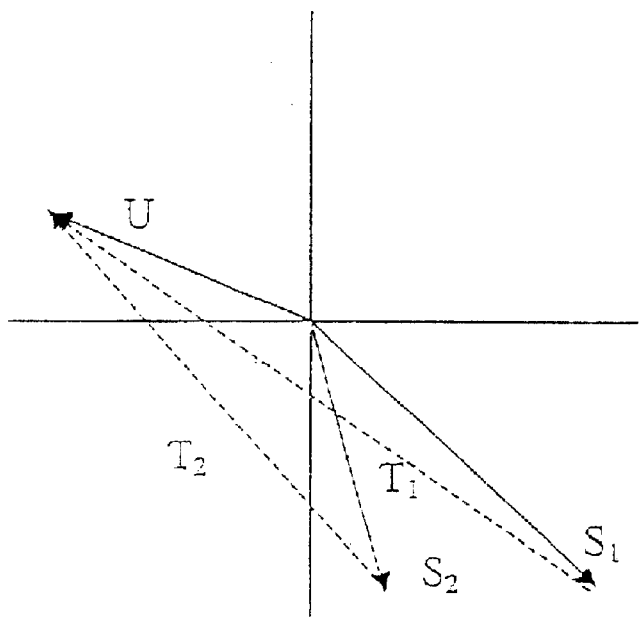
FIG. 3C shows a graphic representation on the complex plane of the complex scattering factors from two adjacent points along a Bragg rod with the CSF of the unknown system approximated as equal.

The second embodiment of the invention applies to systems where the thickness of the unknown 2D structure is small compared to its distance from the surface, $z_0$. In this case, it is possible to determine $U(k_z)$ without measuring the phase derivative. FIGS. 3A–3C are useful in understanding the principle involved.

FIG. 3A is a graphical representation on the complex plane of the known CSF of the ideal substrate, the unknown CSF of the unknown 2D system, and the CSF of the entire sample containing both contributions. From this representation, it is clear that not enough information exists to directly determine the amplitude and phase of the unknown system.

The inclusion of a second nearby point, as illustrated in FIG. 3B, does not provide a solution to the problem. If however, the situation depicted in FIG. 3C can be achieved, then a solution is possible without measuring the phase derivative. Physically, the situation of FIG. 3C is achieved whenever the changes in U are negligibly small compared to the changes in S when moving from a given point on the Bragg rod to a nearby point.

Shifting the zero point of the real-space z-coordinate changes the $k_z$-dependence of $\Phi_U$, $\Phi_Q$, $\Phi_S$. It is easily seen that if the zero point is placed within the unknown 2D layer, then $\Phi_U$ varies with $k_z$ much more slowly than $\Phi_S$.

$$|\Phi_Q| << \Phi_{S_2} - \Phi_{S_1}$$

Thus, $\Phi_Q$ can be well approximated by zero and the complete ratio Q can be approximated with unity. Equations (1) and (2) can now be solved for $U_1$, $\Phi_1$ and $\Phi_2$ and the iteration procedure carried out as described previously. To locate the zero point of the real-space z-coordinate, in order to utilize this embodiment of the invention, it is necessary to either know or approximately guess the position of the 2D layer in the sample. It has been shown in many simulations and measurements that the results obtained from using this method are insensitive to 20% changes in zo (Yacoby Y, et.al. 2000 Direct Structure determination of Systems with two dimensional periodicity. J.Phys: Condens. Matter 12 3929–3938).

This procedure provides U(kz) for all relevant Bragg rods in reciprocal space. Its three-dimensional Fourier back-transformation into real space provides the 3D real-space x-ray dielectric function $\in(\vec{p},z)$ which is related in a known way to the electron-density function. Here, $\vec{p}$ is the position vector in the crystalline-substrate-defined 2D unit cell and z is the distance in the direction normal to the plane of the 2D system.

It is important to notice that the phase at each pair of points along the Bragg rods is determined using information related only to that pair of points. Thus, in contrast to the method of Torrelles et al. (Torrelles X, et. al. 1999 Application of the "direct methods" difference sum function to the solution of reconstructed surfaces Surf. Sci. 423 2–3), computation time is linear in the number of atoms.

The method of the invention is also applicable if the unknown 2D structure is not fully periodic with respect to the 2D grid defined by the underlying substrate crystal. In this case, an average x-ray dielectric function is defined:

Here, $\vec{p}$ is the in-plane vector coordinate within one 2D unit cell defined $$\bar{\varepsilon}(\vec{p},z) = \frac{1}{N}\sum_j \varepsilon(\vec{p}+\vec{r}_j,z). \tag{3}$$

by the substrate crystal and $\vec{r}_j$ is the in-plane coordinate of the jth unit cell. It can be readily shown that the Fourier transform of the averaged dielectric function $\in(\vec{r},z)=\in(\vec{p},z)$ is precisely proportional to the CSF of the system along the Bragg rods. (Notice that in this case, the CSF away from the Bragg rods is non-zero). Thus, measuring the amplitude and phase of the CSF $U(k_\varepsilon, k_\eta, k_z)$ along the Bragg rods and Fourier back-transforming the results into real space directly yields the average dielectric function $\in(\vec{p},z)$. The measurement and the analysis method are the same as for the 2D fully periodic systems.

Although the average dielectric function does not provide the positions of the individual atoms, it does provide the probability of finding an atom of a certain species at a point $(\vec{p},z)$ in the 2D unit cell. For example, if the atoms in a monolayer at a distance z from the surface occupy their ideal positions, $\in(\vec{p},z)$ will have peaks at these positions.

However, if the atoms are displaced due to reconstruction and the unit cell near the interface doubles, $\in(\vec{p},z)$ has double the number of peaks at positions $\vec{p}$ that correspond to the positions in the doubled unit cell projected on the undistorted 2D unit cell defined by the substrate crystal.

Thus, measuring the average dielectric function $\in(\vec{p},z)$ can provide detailed information on the reconstructed structures at interfaces as a function of the distance from the interface.

Measuring $\in(\vec{p},z)$ is also useful in studying crystal-amorphous material interfaces. Close to the interface the crystal is distorted and the electron density is not fully periodic, but it does retain partial periodicity. This periodic component corresponds to the strain-induced displacement of atoms averaged over all 2D unit cells. Furthermore, the crystal induces some degree of order into one or two monolayers of the amorphous material. Thus, measuring $\in(\vec{p},z)$ can provide important information on the local distortions and on the degree of order as a function of the distance from the nominal interface.

Simulations

Figure 1:
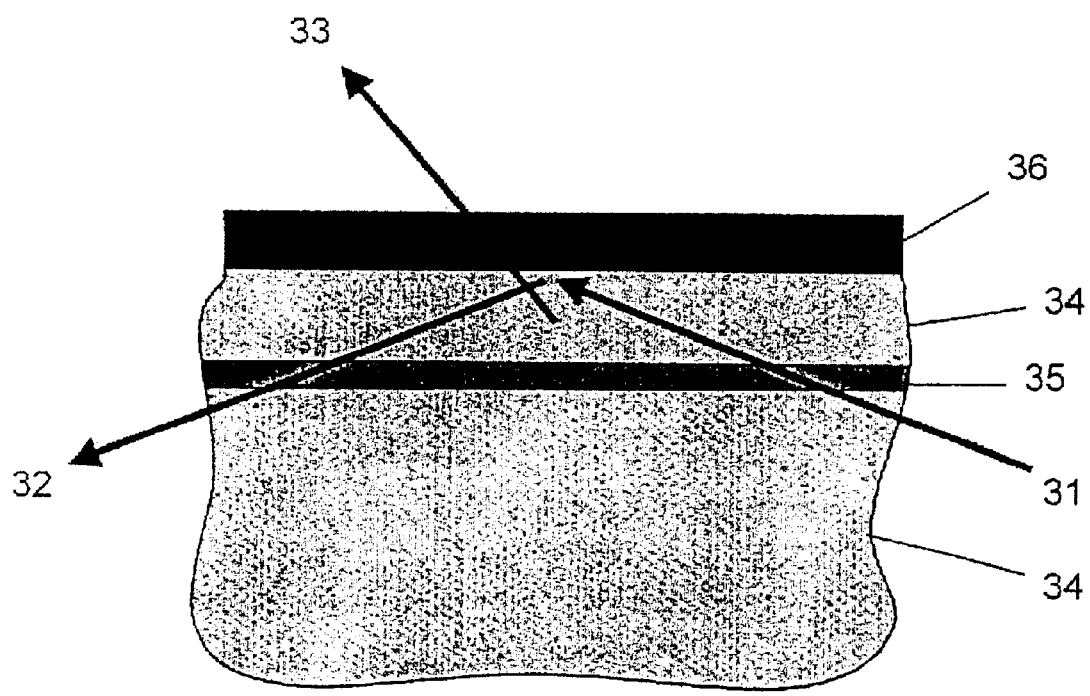
FIG. 1 schematically shows the sample and scattering geometry employed in the method of the invention.

To test the method of the invention, both experiments as well as an extensive set of simulations have been carried out. The simulations all led to the same conclusions, so only a few representative examples of the simulations are presented. These representative simulations all involved a GaAs crystal with a number of AlAs monolayers buried at various distances from the surface. The ALAs monolayers and the crystal surface were assumed to be perpendicular to the (110) direction. It was further assumed that the sample has an evaporated gold layer, as shown in FIG. 1. The diffraction intensity along the Bragg rods was calculated, assuming the scattering geometry shown in FIG. 1, for three x-ray incidence angles $\theta=-0.089°$, $-0.178°$, $-0.355°$. In calculating the diffraction intensity, both the incident x-ray beam and the beam reflected at the sample-gold interface were taken into account. To these simulated data were added noise typical of that encountered in the experiments described further below. From here on, the data were treated as experimental data and the sample as unknown (except for the known ideal crystal). The simulated data were then analyzed in order to recover the sample structure. Using the two-beam diffraction interference method (Baltes H, Yacoby Y, et.al. 1997 Measurement of the X-ray diffraction phase in a 2D crystal Phys. Rev. Lett.79 1285–8), the phase derivative was calculated. The phase itself and the complex scattering factor of the unknown system were obtained using the method described above both with and without the phase derivative. Finally, the CSF was Fourier back-transformed, resulting in the difference between the ideal GaAs electron density and the total electron density of the sample.

Figure 4:
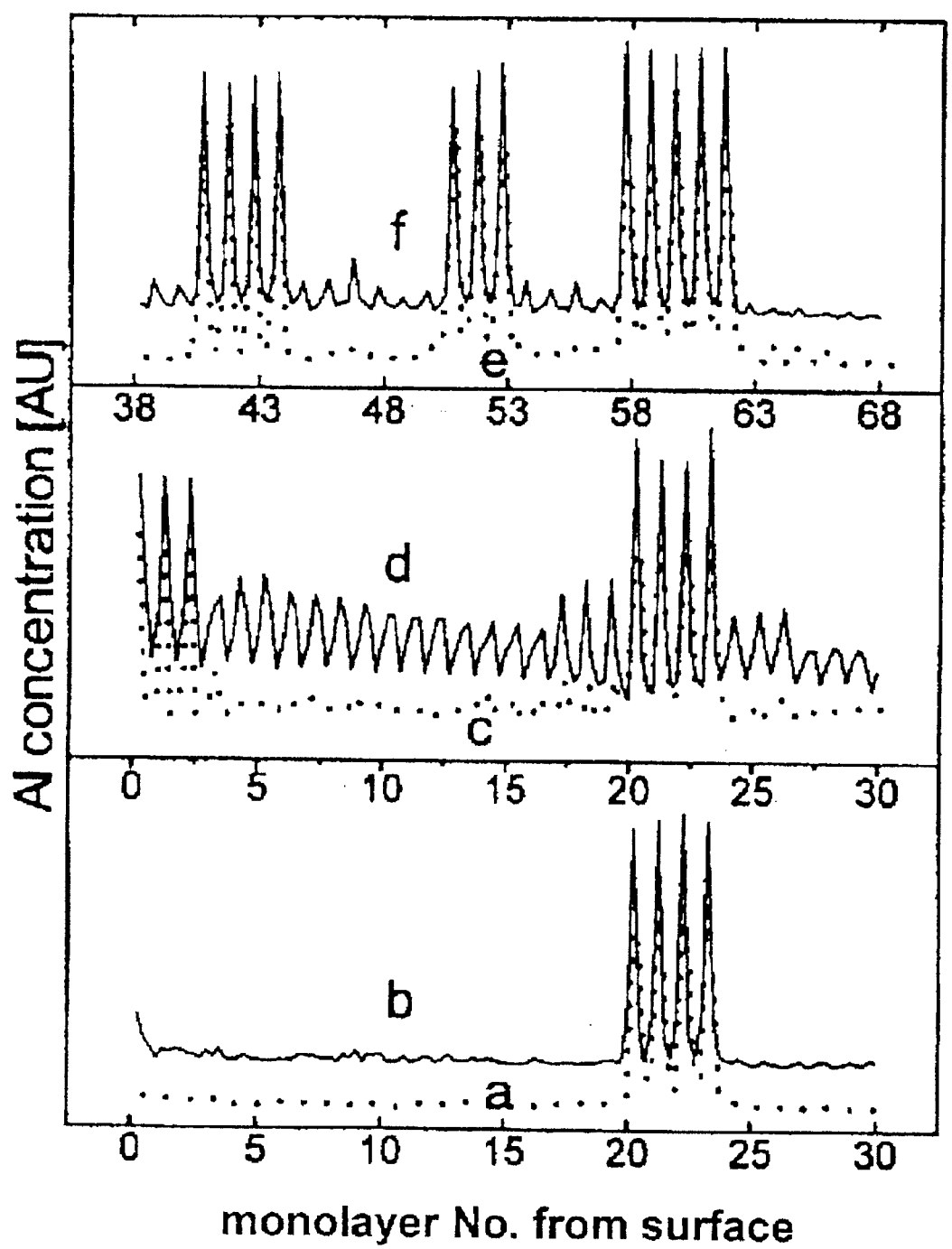
FIG. 4 shows the electron-density differences between an ideal semi-infinite crystal and samples with various numbers and positions of AlAs layers as a function of distance from the sample surface.

In FIG. 4, are presented the results from an analysis of three simulated data sets. The data were simulated along one Bragg rod only: from (−5−1 1) to (1 5 1). The Fourier back-transformation was done in one dimension, yielding the difference between the electron density of the ideal GaAs and the actual sample averaged over each monolayer. Curves a and b show the electron-density difference for a system of four AlAs monolayers buried under twenty monolayers of GaAs analyzed with and without the phase derivative, respectively. As seen, both analyses yield monolayer-resolved structures and very little noise. Curves c and d represent the electron-density difference for a similar structure, but here three AlAs monolayers have been added at the surface. Notice that in this case, the unknown system extends from the surface to 5 nm below it, so its thickness is not small compared to its distance from the surface. Thus, the approximation made in analyzing the data without the phase derivative is not valid. Indeed, as expected, the analysis with the phase derivative gives good results (curve c), while the results obtained without it are rather poor (curve d). Curves e and f show the reconstructed structure of a 22-monolayer thick unknown region buried 40 monolayers beneath the surface. In this case, both embodiments work well. This result shows that the method allows rather thick structurally unknown layers to be reconstructed with monolayer resolution.

Figure 5A:
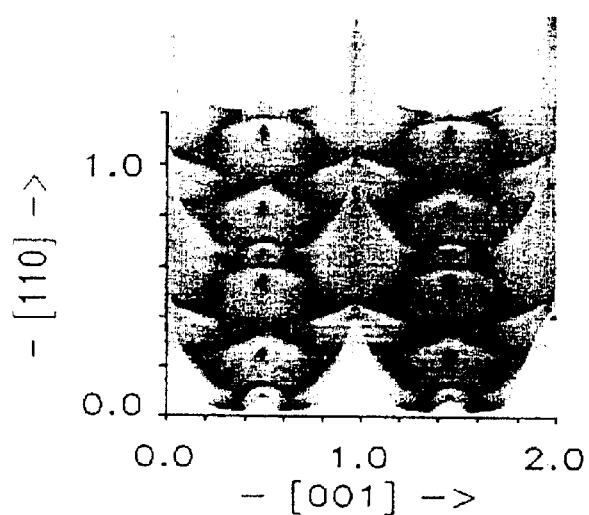
FIGS. 5A and 5B show the electron density difference between an ideal semi-infinite crystal and the sample of FIG. 1 as a function of the in-plane position for two of the monolayers.
Figure 5B:
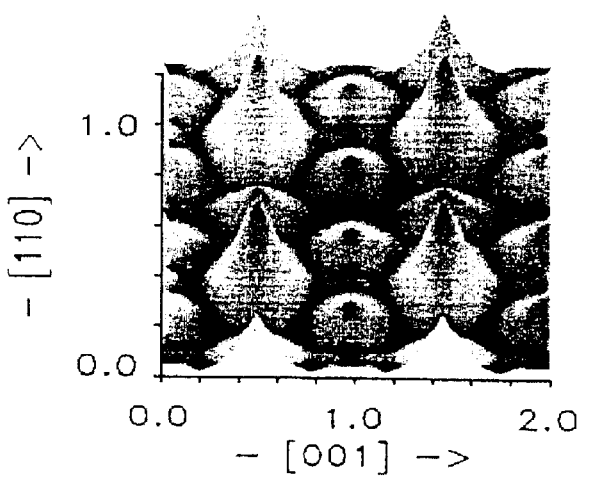

Three-dimensional simulations have also been carried out. In these simulations, the diffraction data along 49 Bragg rods were generated and the data for each rod analyzed as described above. This provided the scattering factor $U(k_{86}, k_\eta, k_z)$, where $k_\xi, k_\eta$ are the x- and y- components of the $(\xi,\eta)$ discrete in-plane reciprocal-lattice vectors. This function was then Fourier back-transformed in three dimensions to obtain the three-dimensional dielectric function. An example of the results is shown in FIGS. 5A and 5B. The structure used was again GaAs with four monolayers of AlAs buried under twenty monolayers of GaAs. In FIG. 5A, the difference between the electron density of pure GaAs and of the sample with AlAs as a function of position in the plane of the AlAs monolayer closest to the surface is shown. The peaks are at the Al-atom positions. The in-plane structure of the next AlAs monolayer is shown in FIG. 5B. As expected, the structure is the same, but shifted by 0.5 and 0.353 unit-cell units in the (001) and (110) directions, respectively. These results show that the structure has been retrieved with both in-plane and out-of-plane atomic resolution.

Experimental demonstration of the method The method has been experimentally demonstrated on two samples. A GaAs crystal was cleaved along a (110) plane in vacuum, in an MBE growth chamber. Four monolayers of AlAs, followed by a cap layer of twenty monolayers of GaAs were nominally grown on it. The number of monolayers was controlled in situ using the usual reflected high-energy electron diffraction (RHEED) method. The crystal was then cleaved into a number of samples. On one of the samples, sample 'b', 200 nm of gold were evaporated, while another, sample 'a', was not coated. Each sample was mounted on a two-axis tilt stage, which was mounted on the φ-circle of a four-circle goniometer. This arrangement allowed scanning of the diffraction intensity along a Bragg rod while keeping the angle of incidence constant. A precision slit (0.5×0.03 mm$^2$) was mounted on the χ-circle of the goniometer along the incident beam path. This allowed the footprint of the incident beam to be minimized. The diffraction intensity was then very carefully measured. Tests showed that the ratio between the diffraction intensities at two points on the same or different Bragg rods could be relied on to within ±2%. This accuracy is crucial in order to obtain good results.

The diffraction profiles were measured along one Bragg rod from (−5 −1 1) to (1 5 1) on beam-line X25 of the National Synchrotron Light Source at Brookhaven National Laboratory. The diffraction from sample 'a' was measured with an angle of incidence of ±0.1°, while sample 'b' was measured for three angles of incidence θ=−0.089°, −0.178°, −0.355°. From these measurements, the phase derivative along the Bragg rod of 'b' was determined, as explained in reference (Baltes H, Yacoby Y, et.al. 1997 Measurement of the X-ray diffraction phase in a 2D crystal Phys. Rev. Lett.79 1285–8). The data were then analyzed using the method discussed above, resulting in the CSF along the Bragg rod. This was then Fourier back-transformed in one dimension, resulting in the difference between in-plane averages of the GaAs and the AlAs electron densities as a function of the distance from the crystal surface.

Figure 6:
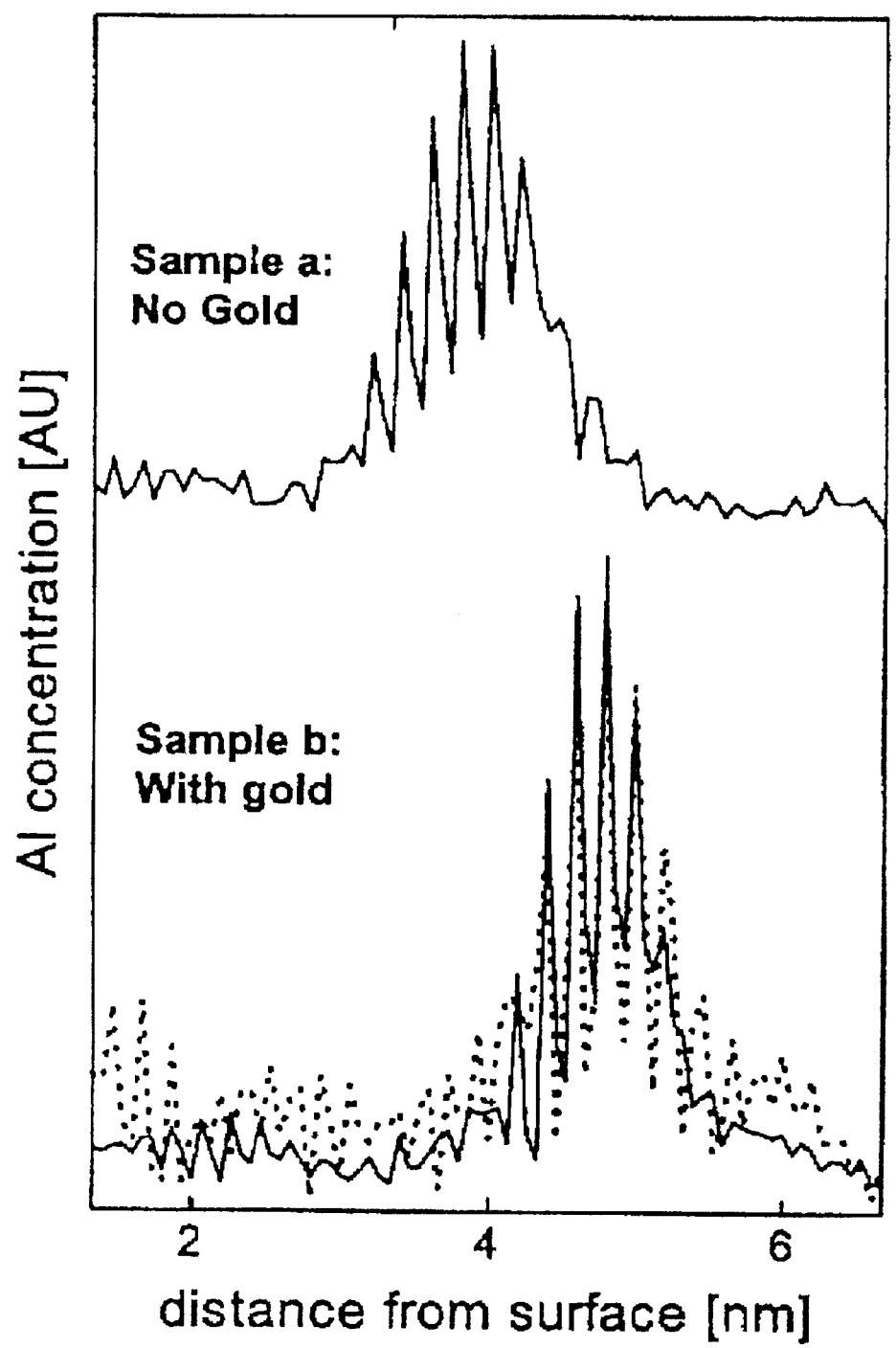
FIG. 6 shows the experimentally obtained electron density difference between an ideal semi-infinite crystal and two samples of the type shown in FIG. 1.

FIG. 6 shows this difference for both samples. Sample 'b' was analyzed using the phase derivative results (first embodiment of the invention), and both samples were also analyzed without the phase derivative using the second embodiment. The solid curves represent the results obtained without the phase derivative, while the dotted line represents the results obtained with it. The results of the two analyses are in good agreement with each other. The electron density obtained with the phase derivative is noisier, because it involves measuring several diffraction profiles at different incidence angles and using differences between the profiles. Each peak corresponds to one monolayer in which the Ga has been partially or fully replaced by Al. The four largest peaks correspond to the four monolayers nominally grown as AlAs. It appears that Al has penetrated into a small number of adjacent nominally GaAs monolayers. This is clearly seen in two monolayers on the left, closer to the surface. The growth seems to have also affected the cleaved crystal, although not to the same extent. The results clearly show that the method of the invention provides the phase along Bragg rods and the structure is obtained with monolayer resolution.

Although embodiments of the invention have been described by way of specific examples, it will be understood that the invention may be carried out with many variations, modifications, and adaptations, without departing from its spirit or exceeding the scope of the claims.

What is claimed is:

1. An x-ray method for the determination of the structure of systems that have two-dimensional periodicity and are positionally correlated with an underlying substrate crystal comprising the following steps:

creating two overlapping x-ray beams in said system having said two-dimensional periodicity such that said overlapping beams propagate at an angle with respect to each other and their orientation relative to said two-dimensional system is such that the diffracted beams interfere with each other;

measuring the diffraction intensity and diffraction interference patterns;

determining the phase derivative of the total complex scattering factor (CSF) along the Bragg rods using the diffraction interference patterns;

determining the CSF along the Bragg rods from the measured diffraction intensity, the phase derivative of the total CSF, and the CSF of the known system;

determining the electron-density function of the layer structure of said system by Fourier transforming the CSF along one Bragg rod;

performing a three-dimensional Fourier back-Transform into real space to provide the three-dimensional real space x-ray dielectric function; and determining the three-dimensional spatial structure, of said system having two-dimensional periodicity from said three-dimensional x-ray dielectric function.

2. An x-ray method for the determination of the structure of systems that have two-dimensional periodicity and are positionally correlated with an underlying substrate crystal according to claim 1, wherein the phase derivative of the total CSF is measured by employing the two-beam diffraction interference method.

3. An x-ray method for direct determination of the structure of systems that have two-dimensional periodicity and are positionally correlated with an underlying substrate crystal according to claim 1, wherein the phase is determined by integration of the measured phase derivative of the CSF.

4. An x-ray method for direct determination of the structure of systems that have two-dimensional periodicity and are positionally correlated with an underlying substrate crystal according to claim 1, wherein the phase is determined by an iterative method using the measured diffraction amplitudes, phase derivatives of the total CSF and the CSF of the known system.

5. An x-ray method for the determination of the structure of systems that have two-dimensional periodicity, or partial two-dimensional periodicity, and are positionally correlated with an underlying substrate crystal according to claim 1, wherein the two overlapping x-ray beams in said structure having said two-dimensional periodicity, or partial two dimensional periodicity, are obtained by total external reflection from a heavy metal film on the sample surface.

6. An x-ray method for the determination of the structure of systems that have two-dimensional periodicity, are positionally correlated with an underlying substrate crystal, and wherein the CSF of the unknown system varies slowly along the Bragg rods compared to that of the known system comprising the following steps:

measuring the diffraction intensity along the Bragg rods;

locating the zero point of the real space z-coordinate such that changes in the CSF of the unknown system for two adjacent points along a Bragg rod are negligible compared to the changes in the CSF of the known system for the corresponding points;

determining the CSF along the Bragg rods from the measured diffraction intensity patterns and the CSF of the known system;

determining the electron-density function of the layer structure of said system by Fourier transforming the CSF along one Bragg rod;

performing a three-dimensional Fourier back-Transform into real space to provide the three-dimensional real space x-ray dielectric function; and determining the three-dimensional spatial structure, of said system having two-dimensional periodicity from said three-dimensional x-ray dielectric function.

7. An x-ray method, according to claim 6, for the determination of the structure of systems that have two-dimensional periodicity, are positionally correlated with an underlying substrate crystal, and wherein the thickness of said unknown structure having two-dimensional periodicity is small compared to its distance from the system surface wherein the zero point of the real space z-coordinate is placed within the unknown system.

8. An x-ray method for the determination of the periodic component of the structure of systems that have partial two-dimensional periodicity, are positionally correlated with an underlying substrate crystal, comprising the following steps:

creating two overlapping x-ray beams in said system having said two-dimensional periodicity such that said overlapping beams propagate at an angle with respect to each other and their orientation relative to said two-dimensional system is such that the diffracted beams interfere with each other;

measuring the diffraction intensity and diffraction interference patterns;

determining the phase derivative of the total complex scattering factor (CSF) along the Bragg rods using the diffraction interference patterns;

determining the CSF along the Bragg rods from the measured diffraction intensity, the phase derivative of the total CSF, and the CSF of the known system;

determining the electron-density function of the layer structure of said system by Fourier transforming the CSF along one Bragg rod;

performing a three-dimensional Fourier back-Transform into real space to provide the three-dimensional real space x-ray dielectric function; and determining the three-dimensional spatial structure, of said system having two-dimensional periodicity from said three-dimensional x-ray dielectric function.

9. An x-ray method for the determination of the structure of systems that have two-dimensional periodicity, or partial two-dimensional periodicity, and are positionally correlated with an underlying substrate crystal according to claim 8, wherein the two overlapping x-ray beams in said structure having said two-dimensional periodicity, or partial two dimensional periodicity, are obtained by total external reflection from a heavy metal film on the sample surface.

10. An x-ray method for the determination of the periodic component of the structure of systems that have partial two-dimensional periodicity, are positionally correlated with an underlying substrate crystal, and wherein the CSF of the unknown system varies slowly along the Bragg rods compared to that of the known system comprising the following steps:

measuring the diffraction intensity along the Bragg rods;

locating the zero point of the real space z-coordinate such that changes in the CSF of the unknown system for two adjacent points along a Bragg rod are negligible compared to the changes in the CSF of the known system for the corresponding points;

determining the CSF along the Bragg rods from the measured diffraction intensity patterns and the CSF of the known system;

determining the electron-density function of the layer structure of said system by Fourier transforming the CSF along one Bragg rod;

performing a three-dimensional Fourier back-Transform into real space to provide the three-dimensional real space x-ray dielectric function; and determining the three-dimensional spatial structure, of said system having two-dimensional periodicity from said three-dimensional x-ray dielectric function.

11. An x-ray method, according to claim 10, for the determination of the periodic component of the structure of systems that have partial two-dimensional periodicity, are positionally correlated with an underlying substrate crystal, and wherein the thickness of said unknown structure having two-dimensional periodicity is small compared to its distance from the system surface wherein the zero point of the real space z-coordinate is placed within the unknown system.

* * * * *